United States Patent [19] [11] 4,219,504
Verbrugge et al. [45] Aug. 26, 1980

[54] PREPARATION OF 2-(2-ACETYL-3-OXOBUTYL)-3,3-DIMETHYL-CYCLOPROPANECARBALDEHYDE

[75] Inventors: Pieter A. Verbrugge; Petrus A. Kramer, both of Amsterdam, Netherlands

[73] Assignee: Shell Oil Company, Houston, Tex.

[21] Appl. No.: 14,529

[22] Filed: Feb. 23, 1979

[30] Foreign Application Priority Data

Mar. 2, 1978 [GB] United Kingdom ............ 832678/78

[51] Int. Cl.$^2$ .............................................. C07C 45/00
[52] U.S. Cl. .................................. 568/365; 560/124; 568/303; 568/338

[58] Field of Search ......................... 260/586 P, 586 R

[56] References Cited

U.S. PATENT DOCUMENTS

| | | | |
|---|---|---|---|
| 3,019,264 | 1/1962 | Eschinazi | 260/586 P |
| 3,023,244 | 2/1962 | Eschinazi | 260/586 P |
| 3,708,528 | 1/1973 | Mukherjee | 260/586 R |

Primary Examiner—Paul J. Killos

[57] ABSTRACT

A process for the preparation of an aldehyde or a ketone by ozonolysis of an ethylenically unsaturated compound in the presence of an anti-oxidant followed by reductive cleavage of the ozonolysis product.

14 Claims, No Drawings

PREPARATION OF 2-(2-ACETYL-3-OXOBUTYL)-3,3-DIMETHYLCYCLOPROPANECARBALDEHYDE

BACKGROUND OF THE INVENTION

1. Field of the Invention

The present invention relates to an improved process for preparing an aldehyde or ketone from an ethylenically unsaturated compound.

2. Description of the Prior Art

The invention relates to an improvement in the prior art process for the preparation of an aldehyde or a ketone by ozonolysis of an ethylenically unsaturated compound with a gaseous mixture comprising ozone and oxygen or air mixture followed by reductive cleavage of the ozonolysis product obtained, and to the aldehydes or ketones so prepared.

The above prior art process often yields appreciable amounts of carboxylic acids and rearrangement products. For example, as described in U.S. Pat. No. 3,708,528, 4-acetyl-2-carene (named hereinafter "compound A").

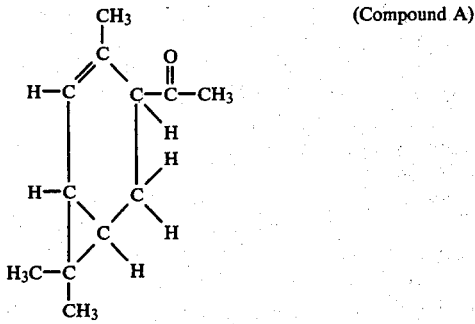
(Compound A)

is ozonolyzed with a gaseous mixture containing ozone and oxygen and the ozonolysis product thus formed is subjected to reductive cleavage with formation of 2-(2-acetyl-3-oxobutyl)-3,3-dimethylcyclopropanecarbaldehyde (named hereinafter "compound B").

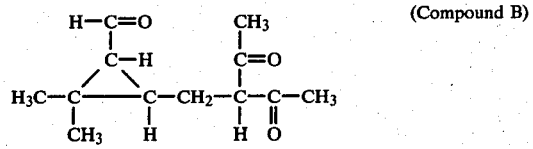
(Compound B)

but analysis by the applicants of the reaction mixture formed by the reductive cleavage has shown that compound B is formed in a low yield, the mixture also containing considerable amounts of 2-(2-acetyl-2-hydroxy-3-oxobutyl)-3,3-dimethylcyclopropanecarbaldehyde (named hereinafter "compound C"),

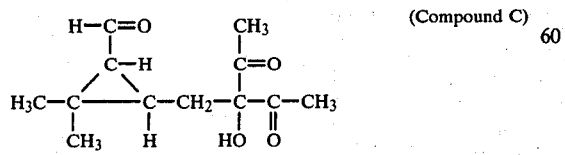
(Compound C)

2-(2-methoxycarbonylpropyl)-3,3-dimethylcyclopropanecarbaldehyde (named hereinafter "compound D")

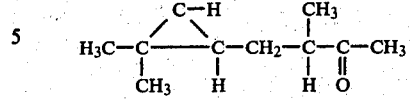
(Compound D)

and 2-(2-acetyl-3-oxobutyl)-3,3-dimethylcyclopropanecarboxylic acid (named hereinafter "compound E").

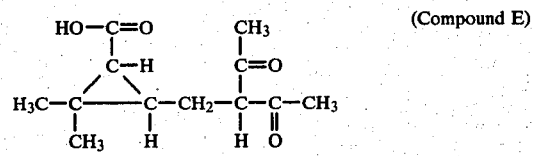
(Compound E)

Thus, compound A is converted by this known process into a complicated mixture of four compounds.

It has now been found that when the ozonolysis is carried out in the presence of a special compound the aldehydes or ketones are usually obtained in an attractively high yield and formation of carboxylic acids and rearrangement products is suppressed.

SUMMARY OF THE INVENTION

Accordingly, the invention provides a process for the preparation of an aldehyde or a ketone by ozonolysis of an ethylenically unsaturated compound with a gaseous mixture comprising ozone and oxygen or air mixture followed by reductive cleavage of the ozonolysis product obtained, which process comprises carrying out the ozonolysis in the presence of an antioxidant. The antioxidant is the special compound referred to hereinbefore.

According to a particularly attractive embodiment of the present invention an aldehyde of the general formula:

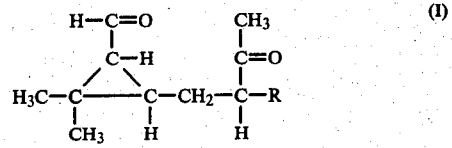
(I)

wherein R represents an organic or inorganic substituent, is prepared by ozonolysis of a 4-substituted-2-carene compound of the general formula:

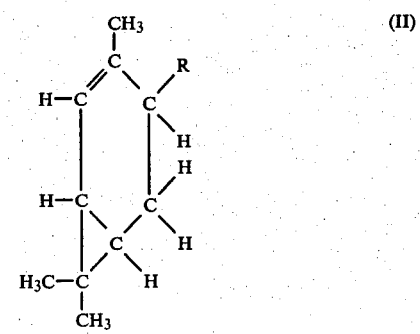
(II)

wherein R has the same meaning as in the general formula I, with a gaseous mixture comprising ozone and oxygen or air mixture in the presence of an anti-oxidant, followed by reductive cleavage of the ozonolysis product obtained.

R represents an organic or inorganic substituent, preferably an alkanoyl group and particularly an alkanoyl group with fewer than five carbon atoms. Most preferably, R represents an acetyl group. Other examples of substituents R are hydroxy, acetoxymethyl, hydroxymethyl, carboxyl and alkyl groups or halogen atoms. The alkyl groups preferably have fewer than five carbon atoms and are most preferably methyl groups.

Any anti-oxidant which does not interfere with reaction is useful. The anti-oxidant may be a sterically hindered phenol, i.e. a phenol having as ortho substituent(s) (a) secondary and/or (a) tertiary hydrocarbyl group(s) containing from 3 to 10 carbon atoms. Examples of such groups are isopropyl, tert-butyl, tert-pentyl, cyclohexyl, norbornyl and isobornyl groups.

The sterically hindered phenols may be mononuclear or polynuclear. Examples of mononuclear phenols are 2,6-di-tert-butylphenol, 2,6-di-tert-butyl-4-methylphenol, 2,4-di-tert-butyl-6-methylphenol, 2,6-diisopropyl-4-methoxymethylphenol; 2,6-di-tert-butyl-4-hydroxymethylphenol, 2,4-dimethyl-6-tert-butylphenol, 2,4,6-tri-tert-butylphenol, 2,6-dicyclohexyl-4-methylphenol, 2,6-dimethyl-4-cyclohexylphenol; 4-methyl-2,6-dioctadecylphenol, 6-(1,1-dimethylhexyl)-2,4-dimethylphenol and 2,6-di-tert-butyl-4-methoxymethylphenol. Examples of polynuclear phenols are biphenols, such as 3,3',5,5'-tetra-tert-butyl-4,4'-dihydroxybiphenyl and 3,3',5,5'-tetraisopropyl-4,4'-dihydroxybiphenyl, and biphenols such as bis(3,5-di-tert-butyl-4-hydroxyphenyl)methane, bis(3-tert-butyl-2-hydroxy-5-methylphenyl)methane and 2,2-di(3,5-di-tert-butyl-4-hydroxyphenyl)propane. Other polynuclear phenolic compounds which can be used in the process according to the invention include the 4,4'-di(3,5-dialkyl-4-hydroxybenzyl)-2,2',3,3',5,5',6,6'-octamethylbiphenyls, such as 4,4'-di(3,5-di-tert-butyl-4-hydroxybenzyl)-2,2',3,3'5,5',6,6'-octamethylbiphenyl, polyphenolic phenols such as 1,3,5-trimethyl-2,4,6-tri(3,5-di-tert-butyl-4-hydroxybenzyl)benzene, 2,4,6-tri(3,5-di-tert-amyl-4-hydroxybenzyl)phenol and 1,1,3-tri(5-tert-butyl-4-hydroxy-3-methylphenyl)butane, and di-(3,5-dialkyl-4-hydroxybenzyl) polynuclear aromatics, such as 9,10-di(3,5-di-tert-butyl-4-hydroxybenzyl)anthracene and 1,4-di(3,5-diisopropyl-4-hydroxybenzyl)naphthalene.

The anti-oxidant used in the process according to the invention may be a derivative of an aromatic amine, such as 1,4-di(sec-butylamino)benzene, N-(4-isopropylaminophenyl)aniline, 1,4-dianilinobenzene, 1-anilinonaphthalene and 2-anilinonaphthalene.

The anti-oxidant may be a heterocyclic compound, such as 6-ethoxy-2,2,4-trimethyl-1,2-dihydroquinoline, 10,10-dimethyl-9,10-dimethyl-9,10-dihydroacridine, benzimidazol, 2-metcaptobenzimidazol and phenothiazine.

The required amount of anti-oxidant usually varies from 0.001 to 10% mol, based on the starting amount of the ethylenically unsaturated compound and preferably from 0.001 to 0.15% mol. However, amounts outside this range are not precluded.

Very good yields of the compounds of formula I are usually obtained when the reaction is carried out in the presence of an alkanol as a solvent. The use of an alkanol provides the possibility of obtaining a dialkyl acetal of the compound of formula I as an end product, which is also within the scope of the present invention. In cases where the aldehyde is the desired end product and an alkanol is used as a solvent a compound preventing acetal formation is suitably used. Examples of compounds preventing acetal formation are basic compounds which do not interfere with the reaction, such as alkali metal carbonates, alkali metal alcoholates and amines, for example potassium carbonate, sodium methoxide and pyridine. Examples of alkanol solvents are methanol, ethanol, propanol and 2-propanol. Very good results have been obtained with methanol.

Examples of other solvents in which the process according to the invention may be carried out are carbon tetrachloride, chloroform, dichloromethane, methyl chloride, ethyl chloride, ethyl acetate, tetrahydrofuran, nitromethane, alkanes with 5 to 10 carbon atoms per molecule, acetone and diethyl ether.

The ozonolysis according to the invention may be carried out at a temperature below $-50°$ C., but such extremely low temperatures are not necessary. Temperatures in the range from $-20°$ C. to $+20°$ C., and particularly from $0°$ C. to $15°$ C., are very suitable.

The gaseous mixture comprising ozone and oxygen is suitably diluted with an inert gas, for example nitrogen or argon or air can be used instead of oxygen.

The reduction of the ozonolysis product to the compound of the general formula II may be carried out with one or more of the many reducing agents known in the art. This reduction may be carried out catalytically, for example, with hydrogen in the presence of a reduction catalyst. Examples of reduction catalysts are noble metals of Group VIII of the Periodic Table of the Elements, supported on a carrier, such as platinum supported on carbon. Other examples of reducing agents are dimethyl sulfide, potassium iodide, stannous chloride and formaldehyde; sodium bisulfite is a useful reducing agent in cases where the aldehyde formed is to isolated.

Compounds of the general formula I are precursors of insecticidally active compounds of the pyrethrin type, for example, as described in U.S. Pat. No. 3,708,528. As these insecticidally active compounds combine exceptionally good insecticidal properties with a very low mammalian toxicity, they are of considerable interest to the agrochemical industry and much effort has been expanded to finding economic routes for their production. Compound A may be prepared by reaction of 3-carene with acetic anhydride in the presence of zinc chloride as described in U.S. Pat. No. 3,708,528. The 3-carene may be optically active and may have the $+$ or $-$ configuration. The (+)-3-carene is a preferred reactant since the products esters are in the (1R,cis) form and usually have the highest pesticidal activity. (+)-3-Carene is an inexpensive, readily available, naturally occurring terpene found in numerous varieties of pine trees, it can be readily purified by fractional distillation. The following Example further illustrates the invention.

EXAMPLE

A 100-ml three-necked flask provided with a magnetic stirrer, a thermometer, a calcium chloride tube and an inlet tube for ozone, was charged with the + configuration of compound A (92 mmol), water-free methanol (60 ml), potassium carbonate powder (0.72 mmol) and the antioxidant 2,2-di(3,5-di-tert-butyl-4-hydroxyphenyl)propane (0.11 mmol) and kept at a temperature between 3° C. and 6° C. Then, a mixture of ozone and oxygen was passed through the liquid in the flask at a rate of 40 l/h, corresponding to 60 mmol of ozone per hour. After 1.75 hours all of the 4-acetyl-2-carene had been converted.

Then, a hydrogenation catalyst (0.5 g) consisting of palladium supported on carbon (10% w of palladium on carbon) was added to the ozonolysis product, the flask was kept at a temperature of 20° C. and hydrogen was passed through the liquid for 2 hours at a rate of 2 l/h. At the end of this period the catalyst was filtered off and washed with diethyl ether (100 ml). The filtrate and washings were combined and washed with three 100-ml portions of water, the washed liquid was dried over anhydrous magnesium sulfate and the solvent was evaporated from the dried liquid, leaving 18.3 g of an oil. Distillation of this oil at a pressure of 32.5 Pa and a temperature of 125° C. afforded compound B in a yield of 66%. Compounds C and D had not been formed and only a trace of compound E was present.

COMPARATIVE EXPERIMENT

The experiment described in the Example was repeated in the absence of 2,2-di(3,5-di-tert-butyl-4-hydroxyphenyl)propane. Compound B was obtained in a yield of less than 27% and considerable amounts of compounds C, D and E had been formed.

We claim:

1. A process for the preparation of an aldehyde of the general formula:

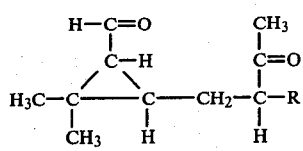

wherein R represents an alkanoyl group containing fewer than five carbon atoms, which comprises ozonolysis of a 4-substituted-2-carene compound of the general formula:

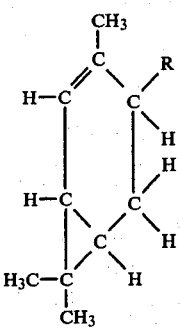

wherein R has the same meaning as in the general formula I, with a gaseous mixture comprising ozone and oxygen in the presence of a sterically hindered phenol or aromatic amine as an antioxidant, followed by reductive cleavage of the ozonlysis product obtained.

2. A process according to claim 1, in which R represents an acetyl group.

3. A process according to claim 1 in which the antioxidant is a sterically hindered phenol.

4. A process according to claim 1, in which the sterically hindered phenol is polynuclear.

5. A process according to claim 4, in which the polynuclear phenol is 2,2-di(3,5-di-tert-butyl-4-hydroxyphenyl)propane.

6. A process according to claim 1 in wihch the antioxidant is present in an amount in the range of from 0.001 to 10% mol, based on the starting amount of the ethylenically unsaturated compound.

7. A process according to claim 1 which is carried out in the presence of an alkanol as a solvent.

8. A process according to claim 7, in which the alkanol is methanol.

9. A process according to claim 7 or 8, which is carried out in the presence of a compound preventing acetal formation.

10. A process according to claim 9, in which the compound preventing acetal formation is an alkali metal carbonate.

11. A process according to claim 1 which is carried out at a temperature in the range of from −20° C. to +20° C.

12. A process according to claim 2 wherein the antioxidant is a polynuclear sterically hindered phenol, the solvent is methanol and an alkali metal carbonate is added to prevent acetal formation.

13. A process according to claim 11 wherein the anti-oxidant is present in a range of from 0.001 to 10% mol, based on the starting amount of the ethylenically unsaturated compound and the reaction is carried out at a temperature in the range of from 0° C. to +15° C.

14. A process according to claim 1 wherein the antioxidant is an aromatic amine.

* * * * *